United States Patent [19]

Takatsu et al.

[11] Patent Number: 5,336,393
[45] Date of Patent: Aug. 9, 1994

[54] PROCESS FOR CATALYTICALLY CONVERTING ORGANIC COMPOUNDS

[75] Inventors: Kozo Takatsu; Yasushi Wakushima; Hiroharu Masunaga; Masahiko Sawa, all of Sodeguara, Japan

[73] Assignee: Idemitsu Kosan Co., Ltd., Tokyo, Japan

[21] Appl. No.: 890,580

[22] Filed: May 28, 1992

[30] Foreign Application Priority Data

Jun. 12, 1991 [JP] Japan .................................. 3-166153
Dec. 11, 1991 [JP] Japan .................................. 3-350480

[51] Int. Cl.⁵ .......................... C07C 2/00; C10G 11/05
[52] U.S. Cl. .................................. 208/120; 585/415; 585/417; 585/418
[58] Field of Search ............. 585/415, 417, 418; 208/120

[56] References Cited

U.S. PATENT DOCUMENTS

| | | | |
|---|---|---|---|
| 4,761,511 | 8/1988 | Barlow | 585/417 |
| 4,861,934 | 8/1989 | Suzuki et al. | 585/417 |
| 5,073,673 | 12/1991 | Hirabayashi et al. | 585/417 |

FOREIGN PATENT DOCUMENTS

| | | |
|---|---|---|
| 0119027 | 9/1984 | European Pat. Off. . |
| 0124271 | 11/1984 | European Pat. Off. . |
| 0215579 | 3/1987 | European Pat. Off. . |
| 2190397 | 11/1987 | United Kingdom . |
| 8504863 | 11/1985 | World Int. Prop. O. . |

OTHER PUBLICATIONS

Chemical Abstracts, vol. 107, No. 1, Jul. 6, 1987, Columbus, Ohio, Abstract No. 10256E, p. 181 of JP-A-62045539.

Chemical Abstracts, vol. 115, No. 20, Nov. 18, 1991, Columbus, Ohio, Abstract No. 211518F, Bandiera Jean et al; "On the enhanced dehydrogenation versus cracking ability of an acidic gallium–MFI: a tentative acid–base interaction model".

*Primary Examiner*—Asok Pal
*Attorney, Agent, or Firm*—Frishauf, Holtz, Goodman & Woodward

[57] ABSTRACT

Catalytic conversion of organic compounds wherein catalysts come into contact with steam is performed efficiently by using a catalyst which comprises an MFI type zeolite having a ratio of $SiO_2/(Al_2O_3+Ga_2O_3)$ of 20 to 200 in molar ratio, a ratio of $Ga_2O_3/Al_2O_3$ of 0 to 50 in molar ratio and a ratio of peak intensity of SiOH, $I_{SiOH}$, to peak intensity of acidic OH, $I_H{}^+$, determined from $^1$H-NMR, $I_{SiOH}/I_H{}^+$, of 0 to 0.5 and loses little catalytic activity on exposure to steam.

27 Claims, No Drawings

PROCESS FOR CATALYTICALLY CONVERTING ORGANIC COMPOUNDS

BACKGROUND OF THE INVENTION (a) Field of the Invention

The present invention relates to a process for catalytically converting organic compounds, particularly to a process wherein a catalyst which loses little activity on contact with steam is used. Useful organic compounds are obtained efficiently by applying the process to various catalytic conversions of organic compounds wherein exposure of catalysts to steam occurs, for example, during the catalytic reactions or regeneration of the catalysts.

(b) Description of the Related Art

Zeolite catalysts show activity in various catalytic conversions of organic compounds and are therefore of great industrial importance. There are various zeolites with various structures and compositions, which have been widely used as catalysts or catalyst ingredients in various catalytic conversions of organic compounds. Among these zeolites of various structures and compositions, recently MFI type zeolites with high silica contents represented by ZSM-5 zeolites have become of interest since they have generally exhibited higher activity, higher selectivity and longer lifetimes in various reactions of organic compounds than those exhibited by other zeolites, including A type, X type and Y type zeolites and mordenite.

Many of the conventional zeolites however show insufficient wet heat resistance, which results in a significant disadvantage of easy lowering of catalytic activity on exposure to steam at high temperature, for example, during catalytic reactions or regeneration. MFI type zeolites with relatively high silica contents, such as ZSM-5, have the same disadvantage so far as those conventionally used and reported teach. Therefore, the lowering of catalytic activity due to exposure to steam has been a serious problem for many methods of catalytically converting organic compounds wherein zeolite catalysts inevitably came into contact with steam at high temperature. The contact between catalysts and steam at high temperature occurs, for example, in reactions wherein formation of an atmosphere of steam is accompanied, including dehydration or conversion of alcohols (e.g. MTG process), reactions accompanying generation of water, such as $CO/H_2$ reactions, reactions using water as a reaction material, such as hydration of olefins, and reactions requiring the presence of water or water-generating ingredients. It should be noted that an atmosphere of steam is also generated during regeneration or pretreatment of catalysts. Even in reactions generating no atmosphere of steam during the reactions, such as catalytic petroleum cracking and conversion of paraffins or olefins, the catalysts are generally regenerated with regeneration gases containing steam to remove carbonaceous matters deposited on the catalysts during the reaction, and come into contact with an atmosphere of a hot steam during the regeneration. This means that a great many processes of catalytically converting organic compounds involve the problem of the lowering of catalytic activity due to such an action of steam.

Further, recently galloaluminosilicates have attracted special interest because of their high catalytic activity exhibited in various catalytic conversions of hydrocarbons, such as aromatization of paraffins or olefins. However, in analogy with the common zeolite catalysts, deposition of coke on the galloaluminosilicate catalysts also occurs during conversion, such as aromatization, of hydrocarbons at high temperature, thereby lowering the catalytic activity. Generally, material hydrocarbons with larger carbon numbers sustain severer lowering of catalytic activity, and olefins are more apt to generate coke than paraffins, thereby causing a severer lowering of catalytic activity. In fact, in case of aromatization of hydrocarbons on galloaluminosilicate catalysts, using very lower paraffins, such as propane or butane, as raw materials does not lower the catalytic activity so considerably. However, using hydrocarbons containing higher paraffins or olefins as raw materials causes severer lowering of activity, so that it becomes very difficult to maintain the initial high activity for more than 100 hours.

Thus, the reactions easily sustaining the lowering of the activity due to the deposition of coke, such as the above-described aromatization, require frequent regenerations of catalysts for burning the coke at high temperatures. With every regeneration, the catalysts are exposed at high temperatures to the steam generated by the burning of coke, and catalysts with poor wet heat resistance lose their activity considerably with every regeneration, so that a considerable decrease in the catalysts' lifetimes on repeated uses becomes a serious problem from the viewpoint of the process efficiency.

The followings are typical examples of the catalytic conversions of organic compounds that involve the problems as described above.

For example, as to the catalytic cracking of gas oil, it was confirmed that a combined use of zeolites (FCC catalysts) having a pore size of more than 7 angstroms with ZSM-5, which is an MFI type zeolite, improves both the octane number and yield of tile obtained gasoline as compared with the use of the former alone [Japanese Patent Application Kokai Koho (Laid-open) No. 47-8074 {Japanese Patent Application Kokoku Koho (Publication) No. 54-37162}]. However, the ZSM-5 synthesized by the method disclosed therein is so poor in wet heat resistance as to lose its activity considerably with every exposure to an atmosphere of steam during regeneration of the catalyst, with the effects of addition thereof lost rapidly. This catalytic conversion process therefore requires continuous addition of ZSM-5, causing use of a large quantity of ZSM-5.

There is a report that as compared with adding small crystals of ZSM-5, adding large crystals of ZSM-5 to FCC catalysts lessens the lowering of activity caused by steaming [Japanese Patent Application Kokai Koho (Laid-open) No. 60-208395]. Nonetheless, the lowering of activity due to the steaming is not yet overcome sufficiently.

In these processes, improving the wet heat resistance of the ZSM-5 would enable addition of the zeolites in a reduced quantity.

There are reported some attempts to improve the wet heat resistance of ZSM-5. For example, in Japanese Patent application Kokai Koho (Laid-open) Nos. 55-51440 and 59-117584 disclosed is that the wet heat resistance of ZSM-5 is improved by introducing metals of Group IB (Cu, Ag), IIB (Zn) or VIII thereto by ion exchange. Nevertheless the improvement is still insufficient, and there arises a problem that the exchanged cations, such as $Ag^+$, lose their effects on reduction thereof.

There is also known a process of producing aromatic hydrocarbons from hydrocarbons, such as paraffins or olefins (particularly $C_5+$ hydrocarbons), by using catalysts containing ZSM-5 [Japanese Patent Application Kokai Koho (Laid-open) No. 49-41322]. In this process, a severe deposition of carbonaceous matters onto the catalysts necessitates frequent regenerations of the catalysts. When the present inventor synthesized the ZSM-5 disclosed in working examples in the specification and used them actually to carry out the same reaction, the catalytic activity was lowered considerably by repeated regenerations by steaming.

It is also reported that zeolites with Ga deposited or ion exchanged thereon exhibit high activity in the above-described aromatization [Japanese Patent Application Kokai Koho (Laid-open) No. 53-92717]. However, there is no teaching how the zeolites were synthesized.

In Japanese patent Application Kokoku Koho (Publication) No. 58-34517 disclosed is a process wherein first gasoline fractions are produced by catalytically cracking a gas oil on cracking catalysts and secondly the ingredients of 4 or less carbon atoms resulting from the cracking and including paraffins and olefins are catalyzed with ZSM-5 to increase the organic content, namely the octane number. The ZSM-5 used were all fresh because of their weakness to wet heat deterioration during regeneration, and the regenerated ZSM-5 were used together with FCC catalysts for the former cracking.

These conventional ZSM-5 are MFI type zeolites. However, as the above-described examples show, although the conventional MFI type zeolites represented by the ZSM-5 are generally effective catalysts or catalyst ingredients for various catalytic conversions of organic compounds, they are so poor in wet heat resistance that there arises a problem that their activity or functions as additive catalysts are easily lowered severely by steaming or by reactions in an atmosphere of steam.

As to the aromatization using galloaluminosilicate catalysts, there have been proposed various techniques. For example, in Japanese Patent Application Kohyo Koho (Laid-open) No. 60-501357 disclosed is increasing the aromatization activity of a galloaluminosilicate by steaming. There is however no description concerning the change of the activity during a long-term steaming (that is, whether the catalytic activity can be maintained sufficiently in spite of the regeneration or repeated regenerations of the catalysts requiring high temperatures and a long-term steaming). Nor is there a description of the variation in the wet heat resistance depending on the preparation methods (synthesizing methods) of the galloaluminosilicate.

In Japanese Patent Application Kokai Koho (laid-open) No. 1-103916 disclosed is obtaining a high yield of of aromatic hydrocarbons from various hydrocarbons by using galloaluminosilicates modified by burning at 700°–1000° C. There is however not described tile change of the activity of the galloaluminosilicates on contact with steam.

That is, these conventional techniques succeeded in providing the galloaluminosilicates exhibiting improved activity in aromatization of hydrocarbons, but are not practical for processes requiring regeneration of catalysts, particularly frequent repetition of reactions and regenerations. The reason is that there is no teaching of the producing methods and compositions that provide galloaluminosilicates having such a high wet heat resistance as to tolerate regeneration or repetition thereof.

It is therefore an important problem to know what producing methods and compositions provide galloaluminosilicates having high catalytic activity and such a high wet heat resistance as to sufficiently tolerate regeneration or repetition thereof.

If galloaluminosilicates having excellent wet heat resistance are found, they will be effective not only for the aromatization of hydrocarbons but also for various reactions catalyzed by other zeolites, such as the ZSM-5. They will be also effective for various processes for catalytic conversion of organic compounds wherein the catalysts necessarily come into contact with steam at high temperature not only during regeneration thereof but also during the reactions (for example, for reactions generating water, such as dehydration of alcohols or hydrogenation of CO, and further for reactions requiring addition of water to material systems).

SUMMARY OF THE INVENTION

An object of the present invention is to provide a process of converting organic compounds which suffer little lowering of activity or functions of catalysts due to contact with steam and is extremely improved in process efficiency.

Based on the inventors' idea that if zeolites losing little activity on exposure to steam at high temperature is used for various catalytic conversions of organic compounds necessitating catalysts to come in contact with steam, the efficiency of the processes may be improved considerably, they studied to improve the wet heat resistance of the conventional MFI type zeolites, such as the conventional ZSM-5. As the result, they found a satisfactory catalyst, which is an MFI type zeolite having a specific composition [$SiO_2/(Al_2O_3+Ga_2O_3)$ and $Ga_2O_3/Al_2O_3$] and a specific characteristic ($I_{SiOH}/I_{H^+}$, namely the ratio of SiOH/acidic OH determined by NMR). This MFI type zeolite is extremely effective for catalytic conversions of organic compounds wherein steam came into contact with catalysts in various manners. On the basis of the finding, the inventors completed the present invention.

That is, the present invention provide a process for catalytically converting an organic compound in the presence of a catalyst including a step wherein the catalyst comes into contact with steam, which process comprises contacting the organic compound with the catalyst, the catalyst comprising an MFI type zeolite, the MFI type zeolite having a ratio of $SiO_2/(Al_2O_3+Ga_2O_3)$ of 20 to 200 in molar ratio and a ratio of $Ga_2O_3/Al_2O_3$ of 0 to 50 in molar ratio and, when the MFI type zeolite is made substantially into an H type zeolite by ion exchange, having a ratio of peak intensity of SiOH, $I_{SiOH}$, to peak intensity of acidic OH, $I_{H^+}$, determined by $^1H$-NMR, $I_{SiOH}/I_{H^+}$, of 0 to 0.5.

PREFERRED EMBODIMENTS OF THE INVENTION

In the process of the present invention, it is important that the MFI type zeolite to be used as a catalyst or a catalyst ingredient for the conversion reaction of the organic compound not only is of MFI type but also has a ratio of $Si_2/(Al_2O_3+Ga_2O_3)$ of 20 to 200 in molar ratio and a ratio of $Ga_2O_3/Al_2O_3$ of 0 to 50 in molar ratio and, when made substantially into an H type zeolite by ion exchange, has a ratio of peak intensity of SiOH, $I_{SiOH}$, to peak intensity of acidic OH, $I_{H^+}$, determined by $^1$H-NMR, $I_{SiOH}/I_H{}^+$, of 0 to 0.5. MFI type zeolites satisfying these conditions are so excellent in wet heat resistance as to lose very little activity on exposure to an atmosphere of steam at high temperatures during reaction or regeneration thereof, and they are very effective catalysts or catalyst ingredients for various catalytic conversions of organic compounds including steps wherein catalysts come into contact with steam. That is, they lose but little activity during reactions carried out in an atmosphere of steam, such as reactions requiring addition of water, and maintain their catalytic activity for a long time. Also, the catalytic activity is not lowered easily by regeneration in an atmosphere of steam, such as a regeneration with a gas containing steam or the removal coke by burning with the air, which accompanies generation of steam. They are therefore also suitable for catalytic conversions of organic compounds which require frequent repetition of such regeneration treatments.

MFI type zeolites having an $SiO_2/(Al_2O_3+Ga_2O_3)$ ratio of less than 20 or more than 200 are insufficient in wet heat resistance or cannot provide sufficient catalytic activity. Particularly, those containing little silica in an $SiO_2/(Al_2O_3+Ga_2O_3)$ ratio of less than 20 may induce considerable deposition of carbonaceous matters, and in any way cannot achieve the object of the present invention.

The preferred range of the $SiO_2/(Al_2O_3+Ga_2O_3)$ ratio cannot be defined uniformly since it depends on the purposes of use, such as the kind of the objective reaction, or operational conditions, such as reaction conditions. From the viewpoint of catalytic activity, it is 20 to 200, preferably 20 to 80.

The molar ratio between the aluminum oxide ingredient and the gallium oxide ingredient contained in the MFI type zeolite, $Ga_2O_3/Al_2O_3$, ranges from 0 to 50, preferably from 0 to 2. In case of using the MFI type zeolite as a galloaluminosilicate containing the gallium oxide ingredient, it is desirable to adjust the $Ga_2O_3/Al_2O_3$ ratio from 0.0001 to 50, preferably from 0.0001 to 2. If the ratio is less than 0.0001, the addition of the gallium oxide ingredient may be of no effect. The presence of the gallium oxide ingredient in a $Ga_2O_3/Al_2O_3$ ratio ranging from 0.0001 to 50 further improves the wet heat resistance and the catalytic activity, particularly the catalytic activity in aromatization of paraffins or olefins.

Herein, the $I_{SiOH}/I_H{}^+$ ratio is the value obtained by carrying out a measurement by $^1$H-NMR as follows.

A zeolite prepared by some method is ion-exchanged substantially completely with a mineral acid, such as hydrochloric acid, or an ammonium salt and is then burned to form an H type zeolite. The H type zeolite is deaerated in vacuum for one hour at 400° C. and is subjected to a measurement of $^1$H-NMR spectrum at room temperature according to a common method. In the obtained NMR spectrum, the peak intensity (peak area) of OH of silanol groups (SiOH) appearing in the vicinity of 1.8 ppm is defined as $I_{SiOH}$, and the peak intensity (peak area) of acidic OH appearing in the vicinity of 4.5 ppm as $I_H{}^+$, and the ratio of $I_{SiOH}/I_H{}^+$ is defined as the $I_{SiOH}/I_H{}^+$ described above.

Herein, "MFI type zeolite having an $I_{SiOH}/I_H{}^+$ ranging from 0 to 0.5" means "MFI type zeolite which will have an $I_{SiOH}/I_H{}^+$ ranging from 0 to 0.5 when modified into H type zeolite", and does not mean that the MFI type zeolite should have this range of $I_{SiOH}/I_H{}^+$ during use thereof. That is, in the present invention, the MFI type zeolite may be used not only as an H type MFI but also in other various forms, for example, by exchanging with ions, such as metallic ions, by making it support various ingredients, by subjecting it to various treatments or by mixing it with other ingredients, as described later. In the latter case, it should be noted that the value of the $I_{SiOH}/I_H{}^+$ is no longer necessarily within the above range.

Even if the $SiO_2/(Al_2O_3+Ga_2O_3)$ ratio ranges from 20 to 200, MFI type zeolites having $I_{SiOH}/I_H{}^+$ of more than 0.5 will be poor in wet heat resistance and will suffer severe lowering of activity on contact with steam. Also its activity itself may be small.

The preferred range of $I_{SiOH}/I_H{}^+$ is from 0 to 0.4.

The crystal structure of the MFI type zeolite is not particularly limited insofar as it is an MFI, and some examples include ZSM-5, ZSM-8, zeta 1, zeta 3, Nu-4, Nu-5, ISI-3, ISI-5, TZ-1, TPZ-1 and TS-1. These MFI type zeolites may be used individually or in a combination thereof by mixing two or more, or may be used as a mixture with other ingredients as described later.

The method of synthesizing the MFI type zeolite to be used in the process of the present invention is not particularly limited, and, for example, generally suitable methods are (a) a method of synthesizing it by using a material mixture consisting essentially of inorganic compounds alone and (b) a method of synthesizing it by using a material mixture consisting essentially of inorganic compounds and an organic compound selected from the group consisting of an alcohol, an amine and an amino-alcohol. Both methods (a) and (b) may be carried out according to common methods in consideration of adjusting the $SiO_2/(Al_2O_3+Ga_2O_3)$ ratio and the $Ga_2O_3/Al_2O_3$ ratio within the specific ranges described above.

In case of the method (a), the MFI type zeolite is synthesized by preparing a material mixture consisting essentially of inorganic compounds alone by using at least one silica source, such as water glass or colloidal silica, and at least one alumina source, such as aluminum sulfate, aluminum nitrate, sodium aluminate, alumina sol or aluminum hydroxide, or at least one silica source, at least one alumina source and at least one gallia source, such as gallium nitrate, gallium sulfate, gallium oxide or gallium metal, and, according to demand, other inorganic additives for adjusting the composition and the liquid properties properly, such as pH, and then subjecting the material mixture to a wet heat reaction at appropriate temperature and pressure.

The method (a) may be carried out in the presence of seed crystals, for example other zeolites, such as mordenite or the above-described MFI type zeolite prepared previously.

In case of the method (b), the MFI type zeolite is synthesized from a material mixture which in addition to at least an silica source and an alumina source or those and at least one gallia source, further contains at least one selected from alcohols, amines and amino-alcohols. Various alcohols may be used as the alcohols, and suitable examples include relatively lower monohydric alcohols, such as n-propanol, ethanol or n-butanol, and relatively lower dihydric and polyhydric alcohols, such as ethylene glycol, propylene glycol or glycerol. Various amines may be used as the amines, and suitable examples include relatively lower primary to tertiary amines, such as morpholine, n-propylamine, tripropylamine, ethylenediamine or pyrrolidine. Various amino-alcohols may be used as the amino-alcohols, and suitable examples include relatively lower amino-alcohols, such as ethanolamine, propanolamine, diethanolamine or triethanolamine. These alcohols, amines and amino-alcohols may be added individually or in a combination of two or more of them. In case of the method (b), according to demand, other organic compounds may be added insofar as the object of the present invention is accomplished.

The method (b) also may be carried out in the presence of seed crystals, for example other zeolites, such as mordenite or the above-described MFI type zeolite prepared previously.

In the methods (a) and (b), particularly preferred silica sources are water glass and colloidal silica, particularly preferred alumina sources are aluminum sulfate and aluminum nitrate, and particularly preferred gallia sources are gallium sulfate and gallium nitrate.

Further, it is also suitable for the methods (a) and (b) to carry out the synthesis by using a material mixture further containing other salts additives, such as sodium chloride.

In many cases, the conventional MFI type zeolites, such as ZSM-5, have been prepared in the presence of quarternary ammonium salts, such as tetrapropylammonium bromide, added as crystallizing agents. According to this method, it is easy to control the $SiO_2/Al_2O_3$ ratio, but it is difficult to control the $I_{SiOH}/I_{H^+}$ within the above-described specific range. Practically, the conventional method provides zeolites, such as ZSM-5, which contain many internal SiOH groups, and the peak intensities $I_{SiOH}$ in their $^1H$-NMR spectra are so large that the values of $I_{SiOH}/I_{H^+}$ exceeds 0.5 even after modification into H type. Such MFI type zeolites are poor in wet heat resistance and lose their activity easily on contact with steam at high temperature. In contrast to this, the inventors found that when synthesis of MFI type zeolite is carried out in the absence of quarternary ammonium compounds, such as tetrapropylammonium bromide, but in the presence of alcohols, such as n-propanol or n-butanol, amines or amino-alcohols or in the absence of any organic compound, the $I_{SiOH}/I_{H^+}$ can be adjusted easily in a wide range including low values. They also found that among thus obtained MFI type zeolites, those which have an $I_{SiOH}/I_{H^+}$ raging from 0 to 0.5 when modified into H type are excellent in wet heat resistance and lose little activity even on use at high temperatures In the presence of steam.

The MFI type zeolite synthesized by the method (a) or (b), according to demand, may be used as a composition containing various additives. For example, they may be made to support various ingredients, for example, various metals or metal compounds, such as Pt, Ni, Ga, Zn, Cu, Co or Fe, $H^+$ sources, such as ammonium ions, or components which become $H^+$ sources, by various supporting techniques, such as ion exchange, impregnation or dipping, or may be mixed with compounds or compositions containing the above-described various elements by, for example, mechanical mixing. According to demand, the MFI type zeolites prepared by the methods described above also may be mixed with other zeolites, and may be molded by using an appropriate binder, such as alumina, silica, silica-alumina, zirconia, magnesia, boria, alumina-boria, titania, silica-titania or clay mineral. The use of appropriate binders further improves the wet heat resistance. It is generally preferable to calcine the MFI type zeolites prepared by the above-described methods at an appropriate temperature prior to use, and calcining them at high temperatures ranging from 400° to 1000° C., preferably from 700° to 1000° C., further improves their catalytic activity. The calcination may be carried out either before or after the addition of above-described additives or the supporting of metal ingredients, or either before or after the composition is molded. Further, according to demand, these zeolites prepared treated with an appropriate treating agent, such as an acid, an alkali, ammonia or halogen, heat or steaming, prior to use.

The MFI type zeolites obtained by the method (a) and the MFI type zeolites obtained by the method (b) may be used as a mixture thereof.

When the MFI type zeolite to be used in the process of the present invention is used as a catalyst or a catalyst ingredient for various catalytic conversion reactions of organic compounds, it not only exhibits an excellent catalytic activity or catalytic functions peculiar to MFI type zeolites but also is so excellent in wet heat resistance that its activity is lowered very little even on exposure to an atmosphere of steam at high temperature during the reactions or regeneration thereof, and its catalytic functions are maintained for a long term. Therefore, by using the MFI type zeolite as a catalyst or a catalyst ingredient, various processes for catalytically converting organic compounds involving steps wherein the catalysts used come into contact with steam can be carried out extremely efficiently and advantageously as compared with the cases where the conventional MFI type zeolites are used.

That is, the process of catalytic conversion of organic compounds of the present invention is not particularly limited so long as it involves some step wherein the catalyst comes into contact with steam, such as the step of catalytic reactions or the step of regenerating the catalyst. The process of the present invention is applicable to various reactions, including reactions wherein the conventional MFI type zeolites have been used as catalysts or catalyst ingredients. It should be noted that the process of the present invention is applicable not only to a process wherein the contact between the catalyst and steam occurs during reactions but also to a process wherein such contact does not occur during reactions but during some other step, for example, during the regeneration or pretreatment of the catalyst.

That is, some examples of the process of the present invention include various processes, for example, (1) processes wherein the catalyst comes into contact with steam during reactions, such as a reaction accompanying generation of water or requiring addition of water to the reaction system as a material or an additive, and (2) processes wherein the catalyst does not necessarily come into contact with steam during catalytic reactions but comes into contact with steam during regeneration of the catalyst. Of course, it is also possible to employ processes wherein the catalyst comes into contact with steam both during reactions and during regeneration, or the catalyst comes into contact with steam during pretreatment thereof.

In case of the processes of the type (1), examples of the catalytic conversion include various dehydrations, such as dehydration of alcohols, various reactions accompanying formation of water, such as conversion of compounds containing oxygen, such as alcohols, to gasoline, and reactions wherein water is used as a reaction material, such as hydration of olefins. Among these, particularly preferred examples are conversion of methanol to gasoline (MTG reaction), conversion of alcohols to gasoline or olefins which accompanies generation of water from the dehydration alcohols, and reactions for synthesizing alcohols by hydrating olefins.

Examples of the catalytic reactions carried out by the processes (2) include various ones, such as catalytic cracking, aromatization, alkylation, disproportionation, polymerization and isomerization of organic compounds, more concrete examples are cracking of hydrocarbons, aromatization of paraffins or olefins, alkylation of hydrocarbons, such as aromatic compounds, paraffins or olefins, with olefins, and disproportionation, isomerization or polymerization of aromatic compounds, paraffins or olefins. Further, the reaction is not limited to a simple reaction but may be a complex reaction involving two or more of the above-described reactions, such as reforming of petroleum distillate.

In these conversions of hydrocarbons, carbonaceous matters (coke) derived from carbon and hydrogen deposit gradually on the catalyst, causing a lowering of the catalytic activity. Therefore, regeneration of the catalyst is repeated at proper intervals. Generally, the regeneration of the catalyst is carried out in the presence of a regeneration gas containing steam and/or oxygen. It should be noted that even if the regeneration gas does not contain steam, the catalyst comes into contact with the steam generated by the combustion of coke with oxygen during the regeneration.

In case of the processes of the type (2), the regeneration of the catalyst is carried out with the catalyst in contact with steam. The regeneration conditions depend on other conditions, such as the catalyst used, the reaction, reaction conditions, reaction time and the process conditions, and generally, the following conditions are suitable for the regeneration of the catalyst.

Suitable regeneration temperature ranges generally from 400° to 850° C., preferably from 500° to 650° C. If the regeneration temperature is lower than 400° C., removal of coke may be insufficient, and if it exceeds 850° C., sintering of the catalyst or destruction of the zeolite framework may occur.

The oxygen concentration in the regeneration gas used for the regeneration is generally 0 to 21% by volume. The steam concentration in the regeneration gas is generally 0 to 30% by volume, preferably 1 to 10% by volume. In order to perform tile regeneration of the catalyst advantageously, it is preferable that the regeneration gas contains one or both of oxygen and steam within the above-described range of concentration. Inert gases, such as nitrogen or carbon dioxide gas, are generally suitable as other gas ingredients contained in the regeneration gas than oxygen and steam, and the regeneration gas may further contain other ingredients according to demand.

The air or a mixed gas of the air and steam is of course suitable as the regeneration gas.

The regeneration conditions described above are particularly suitable for the processes involving the above-described conversions of hydrocarbons.

The interval between regenerations of the catalyst is not particularly limited, but it is generally desirable to repeat the regeneration of the catalyst at intervals of 150 hours or less. The interval of 150 hours or less is particularly desirable for the above-described conversion reactions of hydrocarbons.

A process for aromatization of hydrocarbons, particularly hydrocarbons of 1 to 12 carbon atoms, is suitable for the process of the present invention. More preferable range of the number of the hydrocarbons is from 2 to 10. In this process, coke is deposited in a large quantity, thereby lowering the activity of catalysts severely. It is therefore necessary to send the deteriorated catalyst from the reactor to a regenerator and send back them to the reactor after the coke is burned and removed out. Using the catalyst of the present invention reduces the deterioration of activity and the quantity of flesh catalyst supplied, thereby increasing the efficiency.

Examples of the hydrocarbons to be used as the reaction materials of this process include olefins, paraffins, diene compounds, cycloolefins, cycloparaffins, cyclodiene compounds, or hydrocarbon mixtures containing one of more of them. Although compounds of one carbon atom are difficult to aromatize, no particular problem arises due to the presence thereof in the reaction material.

The reactor suitable for this process is a fluidized bed reactor including reaction/regeneration stages. As the reaction proceeds and aromatic compounds are formed, coke deposits on the catalyst, thereby lowering the activity. Therefore, the deteriorated catalyst is sent continuously from the reactor (fluidized bed) to a regenerator, where the coke is burned and removed out. The catalyst is then sent back into the reactor. This reaction is an endothermic reaction, and circulating the regenerated catalyst heated by the coke's combustion in the regenerator is desirable for maintaining the temperature in the reactor.

The preferred rate of the circulation of the catalyst is such that at least 30 % by weight per hour of the catalyst in the fluidized bed reactor is taken out and is then sent back to the fluidized bed reactor again. At a smaller rate than this, the prevention of deterioration of the catalyst and a sufficient reaction heat supply may become difficult. Water is formed by burning coke in regenerators. The water and heat have changed the structure of the conventional catalysts, thereby reducing the yield of aromatic compounds considerably. However, the catalyst of the present invention is not deteriorated largely by the wet heat, and the reduction in yield is little.

The average density of the fluidized bed suitable for the above-described reaction is from 300 to 500 kg/m$^3$. If it exceeds the range, it may be difficult to change the catalyst, and if less than the range, the reaction may be slowed down. The preferred temperature of the fluidized bed reactor is 350° to 600° C. If it is lower than the range, the yield of aromatic compounds may be reduced. If it is higher than the range, undesirable cracking may increase, and the catalyst may be apt to be deteriorated or damaged. The temperature of the regenerator is not limited, and is preferably 400° to 650° C. If it is lower than the range, regeneration may be insufficient. If it is higher than the range, the catalyst may be apt to be damaged, and further, there may arise an Inconvenience in the energy cost and the balance.

In the process of the present invention, reactions and regeneration described above may be carried out by using various apparatuses and various operations. For example, it is possible to carry out continuous operations or interrupted operations with a static bed apparatus, a fluidized bed apparatus, a moving bed apparatus, a swing type reactor apparatus or a suspension bed apparatus. A batch operation or a semi-batch operation also may be employed. Among these, in the case of the processes (2), particularly the conversion of hydrocarbons described above, it is generally desirable to use a fluidized bed reactor, a moving bed reactor or a swing type reactor, which enables a continuous and effective operation of both of the reactions and regeneration. Reactors used in FCC system are applicable to the fluidized bed reactor. The processes (1) require no particular reactors and may be operated with various reactors. For example, static bed reactors also are suitable.

Hereinafter the present invention will be described in detail with reference to the following Examples and Comparative Examples, which do not limit the scope of the present invention.

EXAMPLES 1 TO 27 AND COMPARATIVE EXAMPLES 1 TO 8

Catalyst Preparation 1

18.8 g of aluminum sulfate (octadecahydrate), 10.9 g of sulfuric acid (97%) and 250 ml of water were mixed to form a solution, which was named liquid-A. 211 g of water glass ($SiO_2$: 29.0% by weight, $Na_2O$: 9.4% by weight, water: 61.6% by weight) and 250 ml of water were mixed to form a solution, which was named liquid-B. 79 g of sodium chloride and 122 ml of water were mixed to form a solution, which was named liquid-C. While the liquid-C was being stirred, the liquid-A and liquid-B were dropped thereto simultaneously and slowly at the room temperature to prepare a material mixture. After addition of 0.5 g of powdery mordenite, the material mixture was adjusted to pH 9.5 with 6 g of a 50% sulfuric acid. The material mixture was then placed in a one-liter autoclave and allowed to react for 20 hours at 170° C. in the sealed autoclave with stirring at 300 r.p.m.

The reaction mixture was cooled and then washed 5 times with 1.5 liter each of water. Subsequently the reaction mixture was filtered to collect solids, which was then dried for 6 hours at 120° C. and further for 6 hours in the air at 550° C.

Thus obtained zeolite was ion exchanged twice each time with 10 ml of 1-N aqueous ammonium nitrate solution per one gram of the zeolite for 4 hours at 80° C. The zeolite was then washed with pure water, dried at 120° C., and calcined for 6 hours at 550° C.

The zeolite was an MFI type zeolite having an $SiO_2/Al_2O_3$ a molar ratio of 29 and a $Ga_2O_3/Al_2O_3$ molar ratio of 0. Hereinafter the zeolite will be called catalyst-A. Measurements on the $^1H$-NMR spectrum of the catalyst-A were made as follows. After 0.18 g of catalyst-A was deaerated for one hour at 400° C. in vacuum and then allowed to cool to the room temperature, the spectrum was measured. The peak area ratio between silanol groups (1.8 ppm) and acidic OH groups (4.5 ppm), $I_{SiOH}/I_{H^+}$, was 0.07.

Catalyst Preparation 2

7.52 g of aluminum sulfate (octadecahydrate), 17.6 of sulfuric acid (97%) and 100 ml of water were mixed to form a solution, which was named liquid-A. 211 g of water glass ($SiO_2$: 29.0% by weight, $Na_2O$:9.4% by weight, water: 61.6% by weight) and 100 ml of water were mixed to form a solution, which was named liquid-B. The liquid-A and liquid-B were dropped to 100 ml of water simultaneously and slowly, to form a mixture. After the mixture was adjusted to pH 9.5 with 6.7 g of 50% sulfuric acid, 180 ml of n-propanol was added to the mixture and mixing was carried out. The resulting aqueous mixture was placed in a one-liter autoclave, and then allowed to react for 48 hours at 150° C. in the sealed autoclave with stirring.

The product was treated in the same manner as in Catalyst Preparation 1 to obtain an H type zeolite. The zeolite was an MFI type zeolite having an $SiO_2/Al_2O_3$ molar ratio of 75 and a $Ga_2O_3/Al_2O_3$ molar ratio of 0. Hereinafter the zeolite will be called catalyst-B.

The $I_{SiOH}/I_{H^+}$ ratio of the catalyst-B was 0.06 as measured in the same manner as in Catalyst Preparation 1.

Catalyst Preparation 3

7.52 g of aluminum sulfate (octadecahydrate), 17.6 of sulfuric acid (97%) and 100 ml of water were mixed to form a solution, which was named liquid-A. 211 g of water glass ($SiO_2$: 29.0% by weight, $Na_2O$: 9.4% by weight, water: 61.6% by weight) and 96 ml of water were mixed to form a solution, which was named liquid-B. The liquid-A and liquid-B were dropped to 50 ml of water simultaneously and slowly, to form a mixture. After the mixture was adjusted to pH 9.5 with 6.8 g of 50% sulfuric acid, 376 ml of n-butanol was added to the mixture and mixing was carried out. The resulting aqueous mixture was placed in a one-liter autoclave, and then allowed to react for 20 hours at 170° C. in the sealed autoclave with stirring.

The product was treated in the same manner as in Catalyst Preparation 1 to obtain an H type zeolite. The zeolite was an ISI-3 type zeolite having an $SiO_2/Al_2O_3$ molar ratio of 73 and a $Ga_2O_3/Al_2O_3$ molar ratio of 0. Hereinafter the zeolite will be called catalyst-C.

The $I_{SiOH}/I_{H^+}$ ratio of the catalyst-C was 0.05 as measured in the same manner as In Catalyst Preparation 1.

Catalyst Preparation 4

Preparation of a crystalline aluminosilicate (H-ZSM-5)

7.52 g of aluminum sulfate (octadecahydrate), 17.6 of sulfuric acid (97%), 26.3 g of tetrapropylammonium bromide and 250 ml of water were mixed to form a solution, which was named liquid-A. 211 g of water glass ($SiO_2$: 2:29.0% by weight $Na_2O$: 9.4% by weight water: 61. 6% by weight) and 250 ml of water were mixed to form a solution, which was named liquid-B. 79 g of sodium chloride and 125 ml of water were mixed to form a solution, which was named liquid-C. The liquid-A and liquid-B were dropped to the liquid-C simultaneously and slowly, to form a mixture. After adjusted to pit 9.5 with 6.0 g of 50% sulfuric acid, the mixture was placed in a one-liter autoclave, and then allowed to react for 20 hours at 170° C. in the sealed autoclave with stirring.

The product was treated in the same manner as in Catalyst Preparation 1 to obtain an H type ZSM-5 zeolite. The zeolite had an $SiO_2/Al_2O_3$ molar ratio of 70 and a $Ga_2O_3/Al_2O_3$ molar ratio of 0. Hereinafter the zeolite will be called catalyst-D.

The $I_{SiOH}/I_{H^+}$ ratio of the catalyst-D was 1.20 as measured In the same manner as in Catalyst Preparation 1.

Catalyst Preparation 5

The same procedure as in Catalyst Preparation 4 was repeated with the exception that the pH was adjusted to 8.2 with 16.0 g of 50% sulfuric acid, to obtain an H type ZSM-5 zeolite having an $SiO_2/Al_2O_3$ molar ratio of 77 and a $Ga_2O_3/Al_2O_3$ molar ratio of 0. Hereinafter the zeolite will be called catalyst-E.

The $I_{SiOH}/I_{H^+}$ ratio of the catalyst-E was 0.85 as measured in tile same manner as in Catalyst Preparation 1.

Examples 1 to 3 and Comparative Examples 1 and 2

Catalytic crackings were carried out in the following conditions by using the catalysts-A, B, C, D and E obtained in Catalyst Preparations 1 to 5 as catalysts. Reaction conditions:

Material: n-hexane, 500° C., atmospheric pressure, WHSV (weight hourly space velocity): 12 hr$^{-1}$, helium/n-hexane molar ratio: 2, Before the catalytic crackings, each catalyst was compression molded to particles of 16 to 32 mesh in particle size. A portion of each catalyst was treated with 2% steam for 120 hours at 600° C. at the atmospheric pressure. Table 1 lists the activity of each of the unsteamed catalysts and the steamed catalysts in cracking the n-hexane.

TABLE 1

| Catalyst | Example Nos. | | | Comparative Example Nos. | |
|---|---|---|---|---|---|
| | 1 A | 2 B | 3 C | 4 D | 5 E |
| Conversion ratio of n-hexane (% by weight) | | | | | |
| Unsteamed catalyst | 95.1 | 82.2 | 80.1 | 77.8 | 62.0 |
| Steamed catalyst | 90.1 | 75.7 | 70.5 | 25.2 | 21.0 |
| K/K$_o$ | 0.77 | 0.82 | 0.76 | 0.19 | 0.24 |

K/K$_o$ = ln (the ratio of the material unchanged by the cracking on steamed catalyst)/ln (the ratio of the material unchanged by the cracking on unsteamed catalyst)

Catalyst Preparations 6 to 16

Zeolites were prepared In the same manner as in Catalyst Preparation 1 with the exception that the materials listed in Table 2 was used in the quantity as listed in Table 2. The catalysts prepared were named F-P respectively, and the measurements of $I_{SiOH}/I_{H^+}$ were carried out in the same manner as in Catalyst Preparation 1. The results are listed in Table 2 and Table 3.

TABLE 2

| Catalyst | Catalyst Preparation Nos. | | | | | |
|---|---|---|---|---|---|---|
| | 6 F | 7 G | 8 H | 9 I | 10 J | 11 K |
| Water glass (g) | 211 | 158 | 211 | 211 | 211 | 211 |
| Al$_2$(SO$_4$)$_3$18H$_2$O (g) | 22.6 | 7.2 | 18.8 | 18.8 | 18.8 | 18.8 |
| H$_2$SO$_4$ (97%) (g) | 13.1 | 12.8 | 13.9 | 13.9 | 13.9 | 12.8 |
| NaCl (g) | 0 | 29.5 | 79.0 | 39.5 | 79.0 | 79.0 |
| Water (ml) | 622 | 732 | 622 | 622 | 622 | 622 |
| Organic additive | — | — | — | — | Morpholine 8.7 g | EtOH 4.7 g |
| Seed crystal | Mordenite 0.5 g | Mordenite 0.38 g | ZSM-5 1.0 g | — | — | — |
| Synthesis | | | | | | |
| Temp. (°C.) | 170 | 170 | 170 | 170 | 170 | 170 |
| Time (hr) | 44 | 44 | 20 | 20 | 20 | 20 |
| SiO$_2$/Al$_2$O$_3$ | 24.5 | 52.2 | 31.2 | 30.4 | 30.1 | 28.2 |
| Ga$_2$O$_3$/Al$_2$O$_3$ | 0 | 0 | 0 | 0 | 0 | 0 |
| Zeolite type | MFI | MFI | MFI | MFI | MFI | MFI |
| $I_{SiOH}/I_{H^+}$ | 0.16 | 0.02 | 0 | 0.14 | 0.30 | 0.08 |

TABLE 3

| Catalyst | Catalyst Preparation Nos. | | | | |
|---|---|---|---|---|---|
| | 12 L | 13 M | 14 N | 15 O | 16 P |
| Water glass (g) | 211 | 158 | 211 | 211 | 211 |
| Al$_2$(SO$_4$)$_3$18H$_2$O (g) | 18.8 | 18.8 | 18.8 | 18.8 | 18.8 |
| H$_2$SO$_4$ (97%) (g) | 12.7 | 12.1 | 15.3 | 12.7 | 12.1 |
| NaCl (g) | 79.0 | 79.0 | 0 | 79.0 | 0 |
| Water (ml) | 622 | 622 | 241 | 622 | 622 |
| Organic additive | DEA 55.0 g | n-PA 11.8 g | n-P 300 g | TPABr 26.3 g | Tn-PA 28.5 g |
| Seed crystal | — | — | — | — | — |
| Synthesis | | | | | |
| Temp. (°C.) | 170 | 170 | 170 | 170 | 170 |
| Time (hr) | 44 | 44 | 20 | 20 | 20 |
| SiO$_2$/Al$_2$O$_3$ | 30.2 | 28.9 | 29.5 | 32.1 | 30.2 |
| Ga$_2$O$_3$/Al$_2$O$_3$ | 0 | 0 | 0 | 0 | 0 |
| Zeolite type | MFI | MFI | MFI | MFI | MFI |
| $I_{SiOH}/I_{H^+}$ | 0.07 | 0.11 | 0.13 | 0.59 | 0.52 |

DEA: diethanolamine, n-PA: n-propylamine, n-P: n-propanol,
TPABr: tetrapropylammonium bromide,
Tn-PA: tri-n-propylamine Examples 4 to 12 and Comparative Examples 3 and 4

N-hexane was catalytically cracked in the same manner as in Example 1 with the exception that each of the H type zeolite catalysts-F-P prepared in Catalyst Preparations 6-16 was used. As in Example 1, there were used unsteamed catalysts and steamed catalysts, respectively. The results are shown in Table 4 and Table 5.

TABLE 4

| Catalyst | Example Nos. | | | | | |
|---|---|---|---|---|---|---|
| | 4 F | 5 G | 6 H | 7 I | 8 J | 9 K |
| Conversion ratio of n-hexane (% by weight) | | | | | | |
| Unsteamed catalyst | 81.7 | 46.5 | 66.4 | 79.5 | 78.0 | 79.5 |
| Steamed catalyst | 41.9 | 39.3 | 36.9 | 51.2 | 62.9 | 66.5 |
| K/K$_o$ | 0.32 | 0.80 | 0.42 | 0.49 | 0.66 | 0.69 |

TABLE 5

| Catalyst | Example Nos. | | | Comparative Example Nos. | |
|---|---|---|---|---|---|
| | 10 L | 11 M | 12 N | 3 O | 4 P |
| Conversion ratio of n-hexane (% by weight) | | | | | |
| Unsteamed catalyst | 84.1 | 86.8 | 75.2 | 74.9 | 85.3 |
| Steamed catalyst | 44.8 | 61.7 | 62.5 | 6.4 | 19.2 |

TABLE 5-continued

| Catalyst | Example Nos. | | | Comparative Example Nos. | |
|---|---|---|---|---|---|
| | 10 L | 11 M | 12 N | 3 O | 4 P |
| $K/K_o$ | 0.32 | 0.47 | 0.70 | 0.05 | 0.11 |

Catalyst Preparation 17

A solution containing 20.8 g of aluminum nitrate (nonahydrate) dissolved in 160 ml of water was added slowly to a solution containing 13.4 g of sodium hydroxide dissolved in 160 ml of water, to form a solution, which was named liquid-A. 200 g of colloidal silica (Trade name: SNOWTEX S) and 250 ml of water were mixed, to form a liquid, which was named liquid-B. A mixture of the liquid-A and liquid-B was prepared by dropping both into a vessel simultaneously, with stirring. The mixture was placed in a one-liter autoclave and then allowed to react for five days at 170° C. with stirring.

The product was treated in the same manner as in Catalyst Preparation 1 to obtain an H type MFI zeolite. The zeolite had an $SiO_2/Al_2O_3$ molar ratio of 28.3 and a $Ga_2O_3/Al_2O_3$ a molar ratio of 0. Hereinafter the zeolite will be called catalyst-Q.

The $I_{SiOH}/I_{H^+}$ ratio of the catalyst-Q was 0.07 as measured in the same manner as in Catalyst Preparation 1.

Example 13

Catalytic crackings of n-hexane were carried out both on the unsteamed catalyst-Q obtained in Catalyst Preparation 17 and on the steamed catalyst-Q. The catalytic crackings and steaming were carried out in the following conditions, and the results are shown in Table 6.

Steaming conditions:
600° C., $H_2O$ concentration: 2%, GHSV (gas hourly space velocity) = 1600 hr$^{-1}$,
treating time: 120 hr
Catalytic cracking of n-hexane:
480° C., 3 ATM, WHSV = 48 hr$^{-1}$,
He/n-hexane molar ratio = 4.0

TABLE 6

| | Unsteamed catalyst-Q | Steamed catalyst-Q | $K/K_o$ |
|---|---|---|---|
| Conversion ratio of n-hexane (%) | 77.4 | 27.1 | 0.21 |

Examples 14 and 15 and Comparative Example 5

The catalysts-A, J and O were impregnated with an aqueous gallium nitrate solution to support 1% by weight of Ga. After drying, the catalysts supporting Ga were calcined for 4 hours at 550° C. and then molded to particles of 16–32 mesh, respectively. Subsequently a portion of each catalyst was steamed in the following conditions. Aromatizations of n-hexane were carried out in the following conditions both on the unsteamed catalysts and on the steamed catalysts. The results are shown in Table 7.

Steaming conditions:
600° C., $H_2O$ concentration: 2%, GHSV = 1600 hr$^{-1}$,
steaming time: 120 hr
Conditions for the aromatization of n-hexane:
500° C., the atmospheric pressure, WHSV = 2 hr$^{-1}$

TABLE 7

| Catalyst | Example Nos. | | Comp. Example Nos. |
|---|---|---|---|
| | 14 A | 15 J | 5 O |
| The quantity of Ga supported (wt %) | 1.0 | 1.0 | 1.0 |
| Unsteamed catalyst | | | |
| Conversion ratio of n-hexane (wt %) | 100 | 100 | 100 |
| Yield of BTX (%) | 49.6 | 45.4 | 46.8 |
| Steamed catalyst | | | |
| Conversion ratio of n-hexane (wt %) | 100 | 100 | 90.7 |
| Yield of BTX (%) | 51.2 | 48.9 | 31.9 |

Catalyst Preparation 18

The catalyst-A (zeolite) obtained previously was impregnated with an aqueous gallium nitrate solution to support 1% by weight of gallium. After drying, the catalyst supporting Ga was calcined for 4 hours at 550° C. and then mixed with alumina as a binder to form a mixture containing 35% by weight of the binder. The mixture was granulated by a spray dryer and then calcined for three hours at 550° C. to form a catalyst-A' for fluidized beds.

Catalyst Preparations 19 and 20

Catalysts-J' and P' for fluidized beds were prepared by using the catalysts-J and P in the same manner as in Catalyst Preparation 18.

Examples 16 and 17 and Comparative Example 6

Aromatizations were carried out in the following conditions by using 100 cc each of the catalysts-A', J' and P', respectively, as a catalyst and by using a fluidized bed reactor equipped with a means for continuous regeneration of catalysts.

(1) Material oil: 50% by weight of DLN+50% by weight of CD5, (paraffins: 74.6% by weight, olefins: 11.3% by weight, diene compounds: 13.5% by weight, others: 0.6% by weight, in total)

| The compositions of the DLN and CD5 | |
|---|---|
| [DLN (desulfurized light naphtha)] | |
| i-pentane | 20.2% by weight |
| n-pentane | 30.5% by weight |
| 2,2-dimethylbutane | 0.5% by weight |
| 2-methylpentane | 15.1% by weight |
| 3-methylpentane | 7.9% by weight |
| n-hexane | 19.5% by weight |
| methylcyclopentane | 6.3% by weight |
| [CD5 (by-product oil fro naphtha thermal cracking)] | |
| 1-butene, isobutylene, 1,3-butadiene | 0.2% by weight |
| trans-2-butene | 0.1% by weight |
| cis-2-butene | 0.2% by weight |
| n-butane | 0.1% by weight |
| neopentane | 0.2% by weight |
| 3-methyl-1-butene | 0.4% by weight |
| unknown | 0.1% by weight |
| 1,4-pentadiene | 2.0% by weight |
| isopentane | 14.0% by weight |
| 1-pentene | 3.0% by weight |
| 2-methyl-1-butene | 3.9% by weight |
| isoprene | 12.9% by weight |
| n-pentane, trans-2-pentene | 24.8% by weight |
| cis-2-pentene | 0.7% by weight |
| 2-methyl-2-butene, trans-1,3-pentadiene | 7.0% by weight |
| cyclopentadiene | 8.0% by weight |
| cis-1,3-pentadiene | 3.2% by weight |
| 2,2-dimethylbutane | 0.1% by weight |
| unknown | 0.1% by weight |

-continued

| The compositions of the DLN and CD5 | |
|---|---|
| cyclopentene | 3.1% by weight |
| cis-4-methyl-2-pentene | 0.5% by weight |
| 2,3-dimethyl-1-butene | 0.3% by weight |
| trans-4-methyl-2-pentene, cyclopentane | 2.8% by weight |
| 2,3-dimethylbutane | 0.1% by weight |
| 2-methylpentane | 3.0% by weight |
| 2-methyl-1-pentene | 0.4% by weight |
| 3-methylpentane | 1.5% by weight |
| unknown | 0.2% by weight |
| n-hexane | 4.1% by weight |
| unknown | 0.3% by weight |
| methylcyclopentane | 0.5% by weight |
| unknown | 0.0% by weight |
| benzene | 1.3% by weight |
| cyclopentadiene | 0.9% by weight |
| Total: | 100% by weight |

(2) Reaction conditions

The temperature in the reactor was 500° C., the temperature in the regenerator was 580° C., the reaction pressure was 0.7 kg/cm$^2$, and the regenerator was fluidized by dry air.

When the value of (the quantity of the catalyst taken out from the reactor per hour)/(the total of the catalyst) is Q, reactions were carried out with Q=20% by weight and Q=40% by weight, respectively, at the supply rate of the material oil of 150 g/hr, and the density of the fluidized bed was adjusted to 400 kg/m$^3$.

(3) Reaction results

The yields of BTX were measured 1, 250 and 500 hours after the reaction conditions had reached the above-described values. The results are listed in Table 8.

TABLE 8

| | | Yield of BTX (% by weight) | | | |
|---|---|---|---|---|---|
| Catalyst Q (wt %) | | 1 hr after | 250 hr after | 500 hr after | Δ BTX 500-1 hr |
| Example 16 | A' | 40 | 53 | 53 | 49 | 4 |
| | | 20 | 53 | 50 | 44 | 9 |
| Example 17 | J' | 40 | 51 | 50 | 46 | 5 |
| | | 20 | 51 | 47 | 40 | 11 |
| Comp. Example 6 | P' | 40 | 52 | 43 | 31 | 21 |
| | | 20 | 52 | 40 | 22 | 30 |

The results listed in Table 8 show that the catalysts-A' and J' having a good wet heat resistance deteriorated little as compared with the catalyst-P', and provided BTX in high average yields during the time from the "1 hr after" to the "500 hr after". Further, a Q of 40% by weight provided BTX in higher average yields during the time from the "1 hr after" to the "500 hr after" as compared with a Q of 20% by weight.

Example 18

Catalyst Preparation 21

(Preparation of catalyst-I made of a galloalumino-silicate)

370 g of aluminum sulfate (octadecahydrate), 116 g of gallium nitrate (nonahydrate), 228 g of sulfuric acid (97% by weight concentration) and 8000 ml of water were mixed to form a solution, which was named liquid-A. 5275 g of water glass (SiO$_2$: 29% by weight, Na$_2$O: 9.4% by weight, water: 61.6% by weight) and 4500 ml of water were mixed to form a solution, which was named liquid-B.

The liquid-A and liquid-B were dropped to 3050 ml of water with stirring. After addition of 12 g of powdery mordenite, the obtained material mixture was adjusted to pH 9.5 with 269 g of 50% sulfuric acid. Thus obtained mixture was placed in a 25-liter autoclave and then allowed to react for 46 hours at 170° C. in the sealed autoclave with stirring at 300 r.p.m. After the reaction, the reaction mixture was cooled to the room temperature and then filtered to collect a solid product. The solid product was washed 5 times with 50 ml each of water per 1 g of the solid product. After washed and filtered thus repeatedly, the solid product was dried for 6 hours at 120° C. and then calcined in the air for 6 hours at 550° C.

Subsequently, the calcined product was subjected to ion exchange twice each time for 4 hours at 80° C. with 10 ml of 1-N aqueous ammonium nitrate solution per 1 g of the calcined product. After dried at 120° C., the ion-exchanged product was calcined in the air for 4 hours at 720° C.

Thus obtained calcined product was identified as an H type MFI galloaluminosilicate having a SiO$_2$/Al$_2$O$_3$ molar ratio of 35.1, an SiO$_2$/Ga$_2$O$_3$ molar ratio of 176, a Ga$_2$O$_3$/Al$_2$O$_3$ molar ratio of 0.2 and an SiO$_2$/(Al$_2$O$_3$+Ga$_2$O$_3$) molar ratio of 29.3. Hereinafter, the calcined product (the H type MFI galloaluminosilicate) will be called galloaluminosilicate-I.

The $I_{SiOH}/I_{H^+}$ ratio of the galloaluminosilicate-I was 0.39 as measured in the same manner as in Catalyst Preparation 1.

In order to use the galloaluminosilicate-I as a catalyst, it was compression molded, ground and sifted through screens, to obtain a catalyst of 16 to 32 mesh in particle size. The catalyst was named catalyst-I.

Reaction 1

(Evaluation of catalytic properties)

Evaluations of the catalytic properties in catalytic conversion of organic compounds were made by carrying out the following catalytic crackings of n-hexane as examples.

Catalytic crackings of n-hexane were carried out by using the catalyst-I obtained in Catalyst Preparation 21 in the conditions of a reaction temperature of 480° C., a reaction pressure of the atmospheric pressure, a WHSV of 48 hr$^{-1}$ and a helium (carrier gas)/n-hexane (raw material) molar ratio of 4. At the time, a portion of the catalyst-I was steamed at 600° C. at the atmospheric pressure in the air containing 2% by volume of steam (GHSV=1600 hr$^{-1}$), and the difference between the steamed catalyst-I and the unsteamed catalyst-I in their activity in cracking n-hexane was investigated. The results are listed in Table 9.

Example 19

Catalyst Preparation 22

(Preparation of catalyst-II made of a galloalumino-silicate)

18.8 g of aluminum sulfate ( octadecahydrate ), 1.4 g of gallium nitrate (nonahydrate), 10.9 g of sulfuric acid (97% by weight concentration) and 250 ml of water were mixed to form a solution, which was named liquid-A. 211 g of water glass (SiO$_2$: 29.0% by weight, Na$_2$O: 9.4% by weight, water: 61.6% by weight) and 250 ml of water were mixed to form a solution, which was named liquid-B. 39.5 g of sodium chloride and 122 ml of water were mixed to form a solution, which was named liquid-C.

While the liquid-C was stirred, the liquid-A and liquid-B were dropped thereto slowly at room temperature and then mixed, to obtain a material mixture. After addition of 0.5 g of powdery mordenite, the material mixture was adjusted to pH 9.5 with 4.5 g of 50% sulfuric acid. The mixture was then placed in a 1-liter autoclave and allowed to react for 20 hours at 170° C. in the sealed autoclave with stirring at 300 r.p.m. After the reaction, the reaction mixture was cooled to the room temperature and filtered to collect a solid product. The solid product was washed 5 times with 50 ml each of water per 1 g of the solid product. After the solid product had been washed and filtered thus, the solid matter obtained was dried for 6 hours at 120° C. and then calcined in the air for 6 hours at 550° C.

Subsequently, the calcined product was subjected to ion exchange twice each time for 4 hours at 80° C. with 10 ml of 1-N aqueous ammonium nitrate solution per 1 g of the calcined product. After dried at 120° C., the ion-exchanged product was calcined in the air for 4 hours at 720° C.

Thus obtained calcined product was identified as an H type MFI galloaluminosilicate having an $SiO_2/Al_2O_3$ molar ratio of 28.1, an $SiO_2/Ga_2O_3$ molar ratio of 625, a $Ga_2O_3/Al_2O_3$ molar ratio of 0.045 and an $SiO_2/(Al_2O_3+Ga_2O_3)$ molar ratio of 26.9. Hereinafter, the calcined product (the H type MFI galloaluminosilicate) will be called galloaluminosilicate-II.

The $I_{SiOH}/I_{H^+}$ ratio of the galloaluminosilicate-II was 0.30 as measured in the same manner as in Catalyst Preparation 1.

In order to use the galloaluminosilicate-II as a catalyst, it was compression molded, ground and sifted through screens, to obtain a catalyst of 16 to 32 mesh in particle size. The catalyst was named catalyst-II.

Reaction 2

(Evaluation of catalytic properties)

Evaluations of the catalytic properties in catalytic conversion of organic compounds were made by carrying out catalytic crackings of n-hexane as examples.

The catalytic crackings of n-hexane and evaluations of the catalytic properties were conducted in the same manner as in Reaction 1 of Example 18 with the exception that the catalyst-II obtained in Catalyst Preparation 22 was used in place of the catalyst-I obtained in Catalyst Preparation 21 of Example 18. The results are listed in Table 9.

Example 20

Catalyst Preparation 23

(Preparation of catalyst-III made of a galloalumino-silicate)

9.67 g of aluminum sulfate (octadecahydrate), 6.07 g of gallium nitrate (nonahydrate), 11.7 g of sulfuric acid (97% by weight concentration) and 250 ml of water were mixed to form a solution, which was named liquid-A. 211 g of water glass ($SiO_2$: 29.0% by weight, $Na_2$: 9.4% by weight, water: 61.6% by weight) and 250 ml of water were mixed to form a solution, which was named liquid-B. 39.5 g of sodium chloride and 122 ml of water were mixed to form a solution, which was named liquid-C.

While the liquid-C was stirred, the liquid-A and liquid-B were dropped thereto slowly at room temperature and then mixed, to obtain a material mixture. After addition of 0.5 g of powdery mordenite, the material mixture was adjusted to pH 9.5 with 5.8 g of 50% sulfuric acid. The mixture was then placed in a 1-liter autoclave and allowed to react for 20 hours at 170° C. in the sealed autoclave with stirring at 300 r.p.m. After the reaction, the reaction mixture was cooled to the room temperature and filtered to collect a solid product. The solid product was washed 5 times with 50 ml each of water per 1 g of the solid product. After the solid product had been washed and filtered thus, the solid matter obtained was dried for 6 hours at 120° C. and then calcined in the air for 6 hours at 550° C.

Subsequently, the calcined product was subjected to ion exchange twice each time for 4 hours at 80° C. with 10 ml of 1-N aqueous ammonium nitrate solution per 1 g of the calcined product. After washed with pure water and dried at 120° C., the ion-exchanged product was calcined in the air for 4 hours at 720° C.

Thus obtained calcined product was identified as an H type MFI galloaluminosilicate having an $SiO_2/Al_2O_3$ molar ratio of 50.3, an $SiO_2/Ga_2O_3$ molar ratio of 118, a $Ga_2O_3/Al_2O_3$ molar ratio of 0.43 and an $SiO_2/(Al_2O_3+Ga_2O_3)$ molar ratio of 35.3. Hereinafter, the calcined product (the H type MFI galloaluminosilicate) will be called galloaluminosilicate-III.

The $I_{SiOH}/I_{H^+}$ ratio of the galloaluminosilicate-III was 0.17 as measured in the same manner as in Catalyst Preparation 1.

In order to use the galloaluminosilicate-III as a catalyst, it was compression molded, ground and sifted through screens, to obtain a catalyst of 16 to 32 mesh in particle size. The catalyst was named catalyst-III.

Reaction 3

(Evaluation of catalytic properties)

Evaluations of the catalytic properties in catalytic conversion of organic compounds were made by carrying out catalytic crackings of n-hexane as examples.

The catalytic crackings of n-hexane and evaluations of the catalytic properties were conducted in the same manner as in Reaction 1 of Example 18 with the exception that the catalyst-III obtained in Catalyst Preparation 23 was used in place of the catalyst-I obtained in Catalyst Preparation 21 of Example 18. The results are listed in Table 9.

Example 21

Catalyst Preparation 24

(Preparation of catalyst-IV made of a galloaluminosilicate)

14.1 g of aluminum sulfate (octadecahydrate), 4.64 g of gallium nitrate (nonahydrate), 9.1 g of sulfuric acid (97% by weight concentration) and 320 ml of water were mixed to form a solution, which was named liquid-A. 211 g of water glass ($SiO_2$: 29.0% by weight, $Na_2O$: 9.4% by weight, water: 61.6% by weight) and 180 ml of water were mixed to form a solution, which was named liquid-B. 79.0 g of sodium chloride and 122 ml of water were mixed to form a solution, which was named liquid-C.

While the liquid-C was stirred, the liquid-A and liquid-B were simultaneously dropped thereto slowly at room temperature and then mixed, to obtain a mixture. After the mixture was adjusted to pH 9.5 with 3.7 g of 50% sulfuric acid, 6.0 g of n-propanol was added thereto, and mixing was carried out. Thus obtained mixture was placed in a 1-liter autoclave and allowed to react for 20 hours at 170° C. in the sealed autoclave with stirring at 300 r.p.m. After the reaction, the reaction mixture was cooled to the room temperature and filtered to collect a solid product. The solid product was washed 5 times with 50 ml each of water per 1 g of the solid product. After the solid product had been washed and filtered repeatedly thus, the solid matter obtained was dried for 6 hours at 120° C. and then calcined in the air for 6 hours at 550° C.

Subsequently, the calcined product was subjected to ion exchange twice each time for 4 hours at 80° C. with 10 ml of 1-N aqueous ammonium nitrate solution per 1 g of the calcined product. After washed with pure water and dried at 120° C., the ion-exchanged product was calcined in the air for 4 hours at 720° C.

Thus obtained calcined product was identified as an H type MFI galloaluminosilicate having an $SiO_2/Al_2O_3$ molar ratio of 32.6, an $SiO_2/Ga_2O_3$ molar ratio of 148, a $Ga_2O_3/Al_2O_3$ a molar ratio of 0.22 and an $SiO_2/(Al_2O_3+Ga_2O_3)$ molar ratio of 26.7. Hereinafter, the calcined product (the H type MFI galloaluminosilicate) will be called galloaluminosilicate-IV.

The $I_{SiOH}/I_{H^+}$ ratio of the galloaluminosilicate-IV was 0.43 as measured in the same manner as in Catalyst Preparation 1.

In order to use the galloaluminosilicate-IV as a catalyst, it was compression molded, ground and sifted through screens, to obtain a catalyst of 16 to 32 mesh in particle size. The catalyst was named catalyst-IV.

Reaction 4

(Evaluation of catalytic properties)

Evaluations of the catalytic properties in catalytic conversion of organic compounds were made by carrying out catalytic crackings of n-hexane as examples.

The catalytic crackings of n-hexane and evaluations of the catalytic properties were conducted in the same manner as in Reaction 1 of Example 18 with the exception that the catalyst-IV obtained in Catalyst Preparation 24 was used in place of the catalyst-I obtained in Catalyst Preparation 21 of Example 18. The results are listed in Table 9.

Example 22

Catalyst Preparation 25

(Preparation of catalyst-V made of a galloalumino-silicate)

14.8 g of aluminum sulfate (octadecahydrate), 4.64 g of gallium nitrate (nonahydrate), 17.6 g of sulfuric acid (97% by weight concentration) and 320 ml of water were mixed to form a solution, which was named liquid-A. 211 g of water glass ($SiO_2$: 29.0% by weight, $Na_2O$: 9.4% by weight, water: 61.6% by weight) and 180 ml of water were mixed to form a solution, which was named liquid-B. 79 g of sodium chloride and 122 ml of water were mixed to form a solution, which was named liquid-C.

While the liquid-C was stirred, the liquid-A and liquid-B were simultaneously dropped thereto slowly at room temperature and then mixed, to obtain a mixture. After the mixture was adjusted to pit 9.5 with 4.4 g of 50% sulfuric acid, 8.7 g of morpholine was added thereto, and mixing was carried out. Thus obtained mixture was placed in a 1-liter autoclave and allowed to react for 20 hours at 170° C. in the sealed autoclave with stirring at 300 r.p.m. After the reaction, the reaction mixture was cooled to the room temperature and filtered to collect a solid product. The solid product was washed 5 times with 50 ml each of water per 1 g of the solid product. After the solid product had been washed and filtered repeatedly thus, the solid matter obtained was dried for 6 hours at 120° C. and then calcined in the air for 6 hours at 550° C.

Subsequently, the calcined product was subjected to ion exchange twice each time for 4 hours at 80° C. with 10 ml of 1-N aqueous ammonium nitrate solution per 1 g of the calcined product. After washed with pure water and dried at 120° C., the ion-exchanged product was calcined in the air for 4 hours at 720° C.

Thus obtained calcined product was identified as an H type MFI galloaluminosilicate having an $SiO_2/Al_2O_3$ molar ratio of 32.6, an $SiO_2/Ga_2O_3$ molar ratio of 148, a $Ga_2O_3/Al_2O_3$ molar ratio of 0.22 and an $SiO_2/(Al_2O_3+Ga_2O_3)$ molar ratio of 26.7. Hereinafter, the calcined product (the H type MFI galloaluminosilicate) will be called galloaluminosilicate-V.

The $I_{SiOH}/I_{H^+}$ ratio of the galloaluminosilicate-V was 0.38 as measured in the same manner as in Catalyst Preparation 1.

In order to use the galloaluminosilicate-V as a catalyst, it was compression molded, ground and sifted through screens, to obtain a catalyst of 16 to 32 mesh in particle size. The catalyst was named catalyst-V.

Reaction 5

(Evaluation of catalytic properties)

Evaluations of the catalytic properties in catalytic conversion of organic compounds were made by carrying out catalytic crackings of n-hexane as examples.

The catalytic crackings of n-hexane and evaluations of the catalytic properties were conducted in the same manner as in Reaction 1 of Example 18 with the exception that the catalyst-V obtained in Catalyst Preparation 25 was used in place of the catalyst-I obtained in Catalyst Preparation 21 of Example 18. The results are listed in Table 9.

Comparative Example 7

Catalyst Preparation CR1

(Preparation of catalyst-CR1 for comparison)

82.6 g of aluminum sulfate ( octadecahydrate ), 75 g of gallium nitrate (octahydrate), 163 g of sulfuric acid (97% by weight concentration), 287 g of tetrapropylammonium bromide and 2700 ml of water were mixed to form a solution, which was named liquid-A. 2326 g of water glass ($SiO_2$: 29.0% by weight, $Na_2O$: 9.4% by weight, water: 61.6% by weight) and 2300 ml of water were mixed to form a solution, which was named liquid-B. 870 g of sodium chloride and 1330 ml of water were mixed to form a solution, which was named liquid-C.

While the liquid-C was stirred, the liquid-A and liquid-B were simultaneously dropped thereto slowly at room temperature and then mixed, to obtain a mixture. After adjusted to pH 9.5 with 8.3 g of 50% sulfuric acid, the mixture was placed in a 25-liter autoclave and allowed to react for 20 hours at 170° C. in the sealed autoclave with stirring at 300 r.p.m. After the reaction, the reaction mixture was cooled to the room temperature and filtered to collect a solid product. The solid product was washed 5 times with 50 ml each of water per 1 g of the solid product. After the solid product had been washed and filtered repeatedly thus, the solid matter obtained was dried for 6 hours at 120° C and then calcined in the air for 6 hours at 550° C.

Subsequently, the calcined product was subjected to ion exchange twice each time for 4 hours at 80° C. with 10 ml of 1-N aqueous ammonium nitrate solution per 1 g of the calcined product. After washed with pure water and dried at 120° C., the ion-exchanged product was calcined in the air for 4 hours at 720° C.

Thus obtained calcined product was identified as an H type ZSM-5 (galloaluminosilicate) having an $SiO_2/Al_2O_3$ molar ratio of 66.7, an $SiO_2/Ga_2O_3$ molar ratio of 113, a $Ga_2O_3/Al_2O_3$ molar ratio of 0.60 and an $SiO_2/(Al_2O_3+Ga_2O_3)$ molar ratio of 41.9. Hereinafter, the calcined product (the HZSM galloaluminosilicate) will be called galloaluminosilicate-CR1.

The $I_{SioOH}/I_{H^+}$ ratio of the galloaluminosilicate-CR1 was 2.8 as measured in the same manner as in Catalyst Preparation 1.

In order to use the galloaluminosilicate-CR1 as a catalyst, it was compression molded, ground and sifted through screens, to obtain a catalyst of 16 to 32 mesh in particle size. The catalyst was named catalyst-CR1.

Reaction CR1

(Evaluation of catalytic properties)

Evaluations of the catalytic properties in catalytic conversion of organic compounds were made by carrying out catalytic crackings of n-hexane as examples.

The catalytic crackings of n-hexane and evaluations of the catalytic properties were conducted in the same manner as in Reaction 1 of Example 18 with the exception that the catalyst-CR1 obtained in Catalyst Preparation CR1 was used In place of the catalyst-I obtained in Catalyst Preparation 21 of Example 18. The results are listed in Table 9.

Example 23

Reaction 6

(Evaluation of catalytic properties)

Evaluations of the catalytic properties in catalytic conversion of organic compounds were made by carrying out the following aromatizations of n-hexane as examples.

Aromatizations of n-hexane were carried out by using the catalyst-I obtained in Catalyst Preparation 21 in the conditions of a reaction temperature of 500° C., a reaction pressure of the atmospheric pressure and a WHSV of 2 $hr^{-1}$. At the time, a portion of the catalyst-I was steamed for 120 hours at 600° C. at the atmospheric pressure in the air containing 2% by volume of steam (GHSV=1600 $hr^{-1}$), and the differences between the steamed catalyst-I and the unsteamed catalyst-I in the conversion ratio of n-hexane and in the yield of BTX were investigated. The results are listed in Table 10.

Example 24

Reaction 7

(Evaluation of catalytic properties)

Evaluations of the catalytic properties in catalytic conversion of organic compounds were made by carrying out aromatizations of n-hexane as examples.

The aromatizations of n-hexane and evaluations of the catalytic properties were conducted in the same manner as in Reaction 6 of Example 23 with the exception that the catalyst-III obtained in Catalyst Preparation 23 of Example 20 was used in place of the catalyst-I obtained in Catalyst Preparation 21 of Example 18. The results are listed in Table 10.

Example 25

Reaction 8

(Evaluation of catalytic properties)

Evaluations of the catalytic properties in catalytic conversion of organic compounds were made by carrying out aromatizations of n-hexane as examples.

The aromatizations of n-hexane and evaluations of the catalytic properties were conducted in the same manner as in Reaction 6 of Example 23 with the exception that the catalyst-IV obtained in Catalyst Preparation 24 of Example 21 was used in place of the catalyst-I obtained in Catalyst Preparation 21 of Example 18. The results are listed in Table 10.

Example 26

Reaction 9

(Evaluation of catalytic properties)

Evaluations of the catalytic properties in catalytic conversion of organic compounds were made by carrying out aromatizations of n-hexane as examples.

The aromatizations of n-hexane and evaluations of the catalytic properties were conducted in the same manner as in Reaction 6 of Example 23 with the exception that the catalyst-V obtained in Catalyst Preparation 25 of Example 22 was used in place of the catalyst-I obtained in Catalyst Preparation 21 of Example 18. The results are listed in Table 10.

Example 27

Catalyst Preparation 26

(Preparation of catalyst-VI made of a galloaluminosilicate)

14.8 g of aluminum sulfate (octadecahydrate), 4.6 g of gallium nitrate (nonahydrate), 9.1 g of sulfuric acid (97% by weight concentration) and 250 ml of water were mixed to form a solution, which was named liquid-A. 211 g of water glass ($SiO_2$: 29.0% by weight, $Na_2O$: 9.4% by weight, water: 61.6% by weight) and 250 ml of water were mixed to form a solution, which was named liquid-B. 79 g of sodium chloride and 122 ml of water were mixed to form a solution, which was named liquid-C.

While the liquid-C was stirred, the liquid-A and liquid-B were simultaneously dropped thereto slowly at room temperature and then mixed, to obtain a mixture. After the mixture was adjusted to pH 9.5 with 5.9 g of 50% sulfuric acid, 55 g of diethanolamine was added thereto, and mixing was carried out. Thus obtained material mixture was placed in a 1-liter autoclave and allowed to react for 20 hours at 170° C. in the sealed autoclave with stirring at 300 r.p.m. After the reaction, the reaction mixture was cooled to the room temperature and filtered to collect a solid product. The solid product was washed 5 times with 50 ml each of water per 1 g of the solid product. After the solid product had been washed and filtered repeatedly thus, the solid matter obtained was dried for 6 hours at 120° C. and then calcined in the air for 6 hours at 550° C.

Subsequently, the calcined product was subjected to ion exchange twice each time for 4 hours at 80° C. with 10 ml of 1-N aqueous ammonium nitrate solution per 1 g of the calcined product. After washed with pure water and dried at 120° C., the ion-exchanged product was calcined in the air for 4 hours at 720° C.

Thus obtained calcined product was identified as an H type MFI galloaluminosilicate having an $SiO_2/Al_2O_3$ molar ratio of 33.8, an $SiO_2/Ga_2O_3$ a molar ratio of 156, a $Ga_2O_3/Al_2O_3$ molar ratio of 0.22 and an $SiO_2/(Al_2O_3+Ga_2O_3)$ molar ratio of 27.8. Hereinafter, the calcined product (the H type MFI galloaluminosilicate) will be called galloaluminosilicate-VI.

The $I_{SiOH}/I_{H^+}$ ratio of the galloaluminosilicate-VI was 0.41 as measured in the same manner as in Catalyst Preparation 1.

In order to use the galloaluminosilicate-VI as a catalyst, it was compression molded, ground and sifted through screens, to obtain a catalyst of 16 to 32 mesh in particle size. The catalyst was named catalyst-VI.

Reaction 10

(Evaluation of catalytic properties)

Evaluations of the catalytic properties in catalytic conversion of organic compounds were made by carrying out the following aromatizations of n-hexane as examples.

The aromatizations of n-hexane and evaluations of the catalytic properties were conducted in the same manner as in Reaction 6 of Example 23 with the exception that the catalyst-VI obtained in Catalyst Preparation 26 was used in place of the catalyst-I obtained in Catalyst Preparation 21 of Example 18. The results are listed in Table 10.

Comparative Example 8

Reaction CR2

(Evaluation of catalytic properties)

Evaluations of the catalytic properties in catalytic conversion of organic compounds were made by carrying out the following aromatizations of n-hexane as examples.

The aromatizations of n-hexane and evaluations of the catalytic properties were conducted in the same manner as in Reaction 6 of Example 23 with the exception that the catalyst-CR1 obtained in Catalyst Preparation CR1 of Comparative Example 7 was used in place of the catalyst-I obtained in Catalyst Preparation 21 of Example 18. The results are listed in Table 10.

TABLE 9

| Catalyst | Example Nos. | | | | | Comp. Ex. No. |
| --- | --- | --- | --- | --- | --- | --- |
| | 18 I | 19 II | 20 III | 21 IV | 22 V | 7 CR1 |
| Conversion ratio of n-hexane (% by weight) | | | | | | |
| Unsteamed catalyst | 67.1 | 70.9 | 52.7 | 78.1 | 65.9 | 57.6 |
| Steamed catalyst | 35.6 | 30.5 | 31.6 | 32.7 | 35.1 | 12.1 |
| $K/K_o$ | 0.40 | 0.30 | 0.51 | 0.26 | 0.40 | 0.15 |

TABLE 10

| Catalyst | Example Nos. | | | | | Comp. Example Nos. |
| --- | --- | --- | --- | --- | --- | --- |
| | 23 I | 24 III | 25 IV | 26 V | 27 VI | 8 CR1 |
| Unsteamed catalyst | | | | | | |
| Conversion ratio of n-hexane (wt %) | 100.0 | 100.0 | 100.0 | 100.0 | 100.0 | 100.0 |
| Yield of BTX (%) | 54.7 | 53.3 | 54.9 | 52.7 | 53.0 | 55.1 |
| Steamed catalyst | | | | | | |
| Conversion ratio of n-hexane (wt %) | 100.0 | 100.0 | 100.0 | 100.0 | 100.0 | 87.9 |
| Yield of BTX (%) | 54.7 | 53.2 | 51.7 | 52.5 | 52.0 | 35.0 |

The results listed in Table 9 show that all the MFI galloaluminosilicate catalysts (catalysts-I-V) used in Examples 18–22, as compared with the conventional ZSM-5 catalyst (catalyst-CR1) used in Comparative Example 7, provided higher $K/K_o$ values, which show their superiority in wet heat resistance and their maintaining high activity in cracking n-hexane even after steaming.

The results listed in Table 10 also show that all the MFI galloaluminosilicate catalysts (catalysts-I and III--VI) used in Examples 23–27 were extremely superior to the conventional ZSM-5 catalyst (catalyst-CR1) used in Comparative Example 8 in wet heat resistance, thereby providing BTX in high yields even after steaming.

As apparent from these results, the specific MFI type zeolite used as a catalyst or a catalyst ingredient in the process of the present invention has both a good catalytic activity and a high wet heat resistance, and the process of the present invention is therefore applicable advantageously not only to the reactions carried out in Examples but also to other various catalytic conversions of organic compounds including a step wherein catalysts come into contact with steam.

What is claimed is:

1. A process for catalytically aromatizing or cracking at least one organic compound not less than five carbon atoms in the presence of a catalyst including a step wherein the catalyst comes into contact with steam, which process comprises contacting the organic compound with the catalyst and regenerating the catalyst at intervals of 150 hours or less, the catalyst comprising an MFI zeolite, the MFI zeolite being synthesized by using a material mixture consisting essentially of inorganic compounds and a zeolite as a seed crystal, the MFI zeolite having a molar ratio of $SiO_2/(Al_2O_3+GaO_3)$ of 20 to 200 and a molar ratio of $Ga_2O_3/Al_2O_3$ of 0 to 50, the MFI zeolite having the characteristic that when the MFI zeolite is formed substantially into an H zeolite by ion exchange, the MFI zeolite has a ratio of peak intensity of SiOH, $I_{SiOH}$, to peak intensity of acidic OH, $I_{H^+}$, determined by $^1$H-NMR, $I_{SiOH}/I_{H^+}$, of 0 to 0.5.

2. The process as claimed in claim 1, wherein the inorganic compounds are at least one silica source selected from the group consisting of water glass and colloidal silica, and at least one alumina source selected from the group consisting of aluminum sulfate, aluminum nitrate, sodium aluminate, alumina sol and aluminum hydroxide.

3. The process as claimed in claim 1, wherein the inorganic compounds are at least one silica source selected from the group consisting of water glass and colloidal silica, at least one alumina source selected from the group consisting of aluminum sulfate, aluminum nitrate, sodium aluminate, alumina sol and aluminum hydroxide and at least one gallia source selected from the group consisting of gallium nitrate, gallium sulfate, gallium oxide and gallium metal.

4. The process as claimed in claim 1, wherein the molar ratio of $SiO_2/(Al_2O_3+Ga_2O_3)$ is 20 to 80 and the molar ratio of $Ga_2O_3/Al_2O_3$ is 0 to 2.

5. The process as claimed in claim 1, wherein the catalyst is the MFI zeolite with at least one metal selected from the group consisting of platinum, nickel, gallium, zinc, copper, cobalt and iron supported thereon.

6. The process as claimed in claim 1, wherein the catalytic conversion is carried out in a reactor selected from the group consisting of a fluidized-bed reactor, a moving-bed reactor and a swing reactor, and the regeneration of the catalyst is carried out at a temperature of 400° to 850° C. with a regeneration gas comprising 0 to 21% by volume of oxygen, 0 to 30% by volume of steam and an inert gas.

7. The process as claimed in claim 1, wherein the process is a catalytic aromatization for producing at least one aromatic compound from at least one hydrocarbon selected from the group consisting of a paraffin of 5 to 12 carbon atoms, an olefin of 5 to 12 carbon atoms, a diene compound of 5 to 12 carbon atoms, a cycloparaffin of 5 to 12 carbon atoms and a cyclodiene compound of 5 to 12 carbon atoms.

8. The process as claimed in claim 1, wherein a reactor selected from the group consisting of a fluidized-bed reactor, a moving-bed reactor and a swing reactor is used.

9. The process as claimed in claim 1, wherein the molar ratio of $SiO_2/(Al_2O_3+Ga_2O_3)$ is 20 to 80; the molar ratio of $Ga_2O_3/Al_2O_3$ is 0 to 2; the ratio $I_{SiOH}/I_{H+}$ is 0 to 0.4; and the MFI zeolite is at least one zeolite selected from the group consisting of ZSM-5, ZSM-8, zeta 1, zeta 3, Nu-4, Nu-5, ISI-3, ISI-5, TZ-1, TPZ-1 and TS-1.

10. The process as claimed in claim 9, wherein the ratio $I_{SiOH}/I_{H+}$ is 0.07.

11. The process claimed in claim 9, wherein the ratio $I_{SiOH}/I_{H+}$ is 0.06.

12. The process as claimed in claim 9, wherein the ratio $I_{SiOH}/I_{H+}$ is 0.05.

13. The process as claimed in claim 9, wherein the ratio $I_{SiOH}/I_{H+}$ is 0.16.

14. The process as claimed in claim 9, wherein the ratio $I_{SiOH}/I_{H+}$ is 0.02.

15. The process as claimed in claim 9, wherein the ratio $I_{SiOH}/I_{H+}$ is 0.14.

16. The process as claimed in claim 9, wherein the ratio $I_{SiOH}/I_{H+}$ is 0.30.

17. The process as claimed in claim 9, wherein the ratio $I_{SiOH}/I_{H+}$ is 0.08.

18. The process as claimed in claim 9, wherein the ratio $I_{SiOH}/I_{H+}$ is 0.07.

19. The process as claimed in claim 9, wherein the ratio $I_{SiOH}/I_{H+}$ is 0.

20. The process as claimed in claim 9, wherein the ratio $I_{SiOH}/I_{H+}$ is 0.11.

21. The process as claimed in claim 9, wherein the ratio $I_{SiOH}/I_{H+}$ is 0.13.

22. The process as claimed in claim 9, wherein the ratio $I_{SiOH}/I_{H+}$ is 0.39.

23. The process as claimed in claim 9, wherein the ratio $I_{SiOH}/I_{H+}$ is 0.17.

24. The process as claimed in claim 1, wherein the ratio $I_{SiOH}/I_{H+}$ is 0.43.

25. The process as claimed in claim 9, wherein the ratio $I_{SiOH}/I_{H+}$ is 0.38.

26. The process as claimed in claim 1, wherein the ratio $I_{SiOH}/I_{H+}$ is 0.41.

27. The process as claimed in claim 7, wherein the catalytic aromatization is carried out in a fluidized-bed reactor with an average fluidized-bed density of 300 to 500 kg/m³, at a temperature of 350° to 600° C., and the catalyst in the fluidized-bed reactor is taken out at a rate of at least 30% by weight per hour to regenerate the catalyst in a regenerator and to return the regenerated catalyst to the fluidized-bed reactor.

* * * * *